(12) United States Patent
Lee et al.

(10) Patent No.: US 10,591,454 B2
(45) Date of Patent: Mar. 17, 2020

(54) HIGHLY SENSITIVE AND SELECTIVE GAS SENSING MATERIAL TO METHYLBENZENE, METHODS FOR PREPARING THE GAS SENSING MATERIAL AND GAS SENSOR INCLUDING THE GAS SENSING MATERIAL

(71) Applicant: Korea University Research and Business Foundation, Seoul (KR)

(72) Inventors: Jong-Heun Lee, Seoul (KR); Jae-Hyeok Kim, Daejeon (KR); Hyun-Mook Jeong, Seoul (KR); Tae-Hyung Kim, Incheon (KR); Hyung-Sik Woo, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 305 days.

(21) Appl. No.: 15/612,510

(22) Filed: Jun. 2, 2017

(65) Prior Publication Data

US 2017/0350871 A1 Dec. 7, 2017

(30) Foreign Application Priority Data

Jun. 3, 2016 (KR) .......................... 10-2016-0069164
May 11, 2017 (KR) .......................... 10-2017-0058608

(51) Int. Cl.
*G01N 33/00* (2006.01)
*C04B 35/42* (2006.01)
*C04B 38/00* (2006.01)
*C04B 35/64* (2006.01)
*C04B 35/626* (2006.01)
(Continued)

(52) U.S. Cl.
CPC ......... *G01N 33/0047* (2013.01); *C04B 35/42* (2013.01); *C04B 35/6267* (2013.01); *C04B 35/64* (2013.01); *C04B 38/009* (2013.01); *C04B 2111/00991* (2013.01); *C04B 2235/3243* (2013.01); *C04B 2235/3284* (2013.01); *C04B 2235/6567* (2013.01); *C04B 2235/662* (2013.01); *C04B 2235/666* (2013.01); *G01N 27/127* (2013.01)

(58) Field of Classification Search
CPC .. G01N 33/0047; G01N 27/127; C04B 35/42; C04B 35/6267; C04B 35/64; C04B 38/009
See application file for complete search history.

(56) References Cited

PUBLICATIONS

Kim et al., "Highly selective and sensitive xylene sensors using Cr2O3—ZnCr2O4 hetero-nanostructures prepared by galvanic replacement," Sensors and Actuators B (2016); 235-498-506.
(Continued)

*Primary Examiner* — Robert J Eom
(74) *Attorney, Agent, or Firm* — Fox Rothschild LLP

(57) ABSTRACT

Disclosed is a gas sensing material for methylbenzene detection. Specifically, the gas sensing material includes a nanocomposite of $Cr_2O_3$ and $ZnCr_2O_4$. The content of Cr in the nanocomposite is from 67.0 at. % to 90.0 at. %, based on the sum of the contents of Cr and Zn atoms. The gas sensing material is highly selective to methylbenzenes over other gases and is highly sensitive to methylbenzenes. Also disclosed are methods for preparing the gas sensing material. The methods facilitate control over the composition of the gas sensing material and enable rapid synthesis of the gas sensing material at low temperature. Also disclosed is a gas sensor including the gas sensing material.

5 Claims, 14 Drawing Sheets

(51) Int. Cl.
*G01N 27/12* (2006.01)
*C04B 111/00* (2006.01)

(56) References Cited

PUBLICATIONS

Hong et al., "One-Pot Synthesis of Pd-Loaded SnO2 Yolk-Shell Nanostructures for Ultraselective Methyl Benzene Sensors," Chem. Eur. J. (2014); 20:2737-2741.

HIGHLY SENSITIVE AND SELECTIVE GAS SENSING MATERIAL TO METHYLBENZENE, METHODS FOR PREPARING THE GAS SENSING MATERIAL AND GAS SENSOR INCLUDING THE GAS SENSING MATERIAL

BACKGROUND OF THE INVENTION

1. Field of the Invention

The present invention relates to a gas sensing material for detecting methylbenzenes, methods for preparing the gas sensing material, and a gas sensor including the gas sensing material.

2. Description of the Related Art

Some indoor environmental gases are volatile organic compounds known to be harmful to humans. Such volatile organic compounds are mostly colorless, odorless, and exist as gases at room temperature, making their presence difficult to detect. Representative toxic volatile organic compounds include benzene, toluene, xylene, alcohols, and formaldehyde. However, most oxide semiconductor gas sensors exhibit similar sensitivities to these gases or are highly sensitive to alcohols only. Volatile organic compounds have their recommended lower concentration limits for detection, have different influences on human health, and cause different diseases in humans. For these reasons, there is a need for gas sensors that are selectively sensitive to individual gases.

There is also a need for gas sensors that can selectively detect indoor organic compounds that are present in very small amounts, particularly, methylbenzenes such as toluene and xylene, to measure indoor pollution levels. To meet these needs, the following detailed technical requirements should be taken into account.

First, gas sensors are required to determine an environment where methylbenzenes are released at a concentration of 10 ppm for 10 minutes as a serious indoor pollution level, as recommended by the U.S. Occupational Safety and Health Administration. Humans may suffer from nausea, dizziness, ocular diseases, and dermal diseases when exposed to methylbenzenes at a higher concentration than the recommended one or for a longer time than the recommended one. Thus, materials highly sensitive to methylbenzenes at a concentration much lower than 10 ppm are needed.

Second, alcohol gases are frequently produced by various causes, for example, cooking, air freshener spraying, and drinking. Accordingly, sensors for detecting environmental pollutants should necessarily have low sensitivity to alcohols in order to prevent their malfunction. Gas sensors should be prevented from malfunction due to interference gases, such as carbon monoxide and formaldehyde, that are present indoors and in cars. Thus, there is a need for gas sensing materials whose selectivity to methylbenzenes is several times higher than that to interference gases, such as alcohols, monoxide and formaldehyde, in order to prevent malfunction caused by noise gases that are continuously released in the indoor environment.

Third, it is important to choose appropriate structures and synthetic methods of sensing materials that are effective in enhancing the sensitivity and selectivity of the sensing materials to methylbenzene gases. Particularly, when a sensing material adopts a heterojunction structure in which an oxide coated with a catalytic material or two or more oxides form an interface, it exhibits maximized catalytic activity for gas reforming/oxidation/decomposition, and as a result, its sensitivity and selectivity to methylbenzenes can be effectively improved. A change in the resistance of the sensing material can be maximized through control over the concentration of charge carriers in the sensing material so that the sensitivity and selectivity of the sensing material to methylbenzenes can be effectively improved. Such effects can be utilized through general processes for the synthesis of sensing materials, such as vapor-liquid-solid, sputtering, e-beam, and liquid coating processes. However, these processes suffer from difficulty in quantifying the modification of sensing materials and are disadvantageous in terms of cost, making them difficult to commercialize.

Particularly, pure $Cr_2O_3$ and single-phase $ZnCr_2O_4$ fine powders are necessary for the synthesis of a sensing material (such as a $Cr_2O_3/ZnCr_2O_4$ nanocomposite) having a heterojunction structure in which two or more oxides with good catalytic activity are uniformly mixed, as in the present invention. However, the preparation of the single-phase $ZnCr_2O_4$ fine powder requires a solid-state reaction of a mix of ZnO and $Cr_2O_3$ fine powders, followed by annealing at least 1100° C., However, this procedure is very energy-consuming and require additional processes and much time. Other problems are the large size and small surface area of $ZnCr_2O_4$ particles, leading to low sensitivity of the gas detection material. Although a single-phase $ZnCr_2O_4$ fine powder is successfully synthesized, it is difficult to synthesize a homogeneous $Cr_2O_3/ZnCr_2O_4$ nanocomposite by a solid-state reaction method. Thus, effective design of a gas sensor for the detection of environmental pollutants requires an effective method for synthesizing a detecting material that has the advantages of low cost, energy, and time consumption, is small in particle size, and is composed of dissimilar oxides with good interfacial contact.

In this connection, many approaches have recently been proposed to activate selective gas detection, for example, by adding and coating oxide semiconductors with dissimilar oxides or noble metals with good catalytic activity for the detection of particular gases for the preparation of gas sensing materials capable of selectively detecting particular substances (H.-J. Kim, ACS Appl. Mater. Inter. 6 (2014) 18197-18204; S.-J. Hwang, Chem. Eur. J. 21 (2015) 5872-5878; and H.-M. Jeong, Sens. & Actuat. B 201 (2014) 482-489). In addition to these approaches, proposals have been made on additional processes for increasing selectivity by attaching specially designed gas filters to gas sensors (M. Fleischer, Sens. & Actuat. B 69 (2000) 205-210; and A. Cabot, Thin Solid Films 436 (2003) 64-69).

However, the conventional methods suffer from difficulty in optimizing and quantifying the amount of catalysts added. Other disadvantages of the conventional methods are that additives are difficult to homogenize and an improvement in selectivity to a single gas is little or the additional processes create an economic burden. Particularly, the conventional methods fail to provide sensing materials that show high selectivities to target gases over interference gases. For example, sensing materials prepared by the conventional methods have a disadvantage in that it is difficult to selectively detect gas molecules, such as methylbenzenes (xylene and toluene) and benzene, that have a benzene ring and are similar in molecular structure.

SUMMARY OF THE INVENTION

The present invention has been made in view of the problems of the prior art, and it is an object of the present invention to provide a gas sensing material capable of detecting methylbenzenes belonging to indoor environmental gases with high sensitivity and high selectivity, methods for preparing the gas sensing material, and a gas sensor including the gas sensing material.

One aspect of the present invention provides a gas sensing material for methylbenzene detection, including a nanocomposite of $Cr_2O_3$ and $ZnCr_2O_4$ wherein the content of Cr in the nanocomposite is from 67.0 at. % to 90.0 at. %, based on the sum of the contents of Cr and Zn atoms.

A further aspect of the present invention provides a method for preparing a gas sensing material for methylbenzene detection, including a) preparing a solution including a Zn salt and a carbohydrate, b) subjecting the solution to spray pyrolysis to prepare a ZnO powder having a hollow structure, and c) mixing the ZnO powder with a Cr salt, followed by a galvanic replacement reaction to produce a nanocomposite of $Cr_2O_3$ and $ZnCr_2O_4$.

According to another embodiment of the present invention, step c) may include i) dissolving the ZnO powder in xylene and heating the solution to 80° C. to 150° C., ii) adding oleylamine and oleic acid to the heated solution and stirring the resulting solution, iii) mixing the stirred solution with a Cr salt, followed by a galvanic replacement reaction.

According to another embodiment of the present invention, the method may further include, after step c), washing and drying the $Cr_2O_3/ZnCr_2O_4$ nanocomposite and annealing the dried $Cr_2O_3/ZnCr_2O_4$ nanocomposite at 400° C. to 700° C. for 0.2 hours to 16 hours.

Another aspect of the present invention provides a method for preparing a gas sensing material for methylbenzene detection, including a) mixing a Zn salt powder with a Cr salt powder and subjecting the powder mixture to ball milling to prepare a mixed powder and b) calcining the mixed powder at 1100° C. to 1300° C. for 6 hours to 8 hours to prepare a solid-state mix in the form of a fine powder.

Another aspect of the present invention provides a gas sensor for methylbenzene detection, including a gas sensing layer composed of the gas sensing material.

Yet another aspect of the present invention provides a method for fabricating a gas sensor for methylbenzene detection, including a) mixing the gas sensing material with deionized water to prepare a paste, b) coating the paste on a substrate, and c) drying and annealing the coated substrate to form a gas sensing layer.

The gas sensing material of the present invention is highly selective to methylbenzenes over other gases and is highly sensitive to methylbenzenes. In addition, the methods for preparing the gas sensing material according to the present invention facilitate control over the composition of the gas sensing material and enable rapid synthesis of the gas sensing material at low temperature.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE INVENTION

The present invention will now be described in more detail.

The present invention is directed to a gas sensing material for the detection of methylbenzenes as major indoor environmental pollutant gases with very high sensitivity and outstanding selectivity, methods for preparing the gas sensing material, and a gas sensor including the gas sensing material.

A gas sensing material for methylbenzene detection according to the present invention includes a nanocomposite of $Cr_2O_3$ and $ZnCr_2O_4$. Particularly, the content of Cr in the nanocomposite is from 67.0 at. % to 90.0 at. %, based on the sum of the contents of Cr and Zn atoms.

The $Cr_2O_3$ content of the $Cr_2O_3/ZnCr_2O_4$ nanocomposite is a very important factor determining the sensitivity and selectivity of the gas sensing material. It is thus important to quantitatively control the $Cr_2O_3$ content.

If the content of Cr in the nanocomposite is less than 78.2 at. %, the gas responses of the gas sensing material to methylbenzene gases and the selectivities of the gas sensing material to methylbenzene gases over other gases may be lowered, which can be seen from the results in Examples 1 to 3 that follow. Meanwhile, if the content of Cr in the nanocomposite exceeds 90.0 at. %, the proportion of $Cr_2O_3$ increases over the entire region of the sensing material, and as a result, the gas response of the sensing material to methylbenzene gases is lowered because electric conduction occurs through $Cr_2O_3$ with the lower resistance and gas response.

As can be seen from the results in Example 4 that follows, a $Cr_2O_3/ZnCr_2O_4$ composite containing 68.0 at. % of Cr can be synthesized based on spray pyrolysis. Also in this case, the composite has high response and selectivity to methylbenzenes, indicating its applicability to a methylbenzene gas sensor even when the Cr content is 68.0 at. %.

Therefore, the $Cr_2O_3$ content of the $Cr_2O_3/ZnCr_2O_4$ nanocomposite in the gas sensing material for methylbenzene detection according to the present invention may be from 67.0 at. % to 90.0 at. %.

The present invention also provides methods for preparing the gas sensing material for methylbenzene detection. Various methods for the production of the $Cr_2O_3/ZnCr_2O_4$ nanocomposite satisfying the composition defined above can be used to prepare the gas sensing material for methylbenzene detection according to the present invention. Particularly, a method based on galvanic replacement is advantageous in terms of continuous composition control. Another advantage is that homogeneous composites composed of two or more components at a molecular level can be rapidly synthesized at low temperature.

Figure 1:
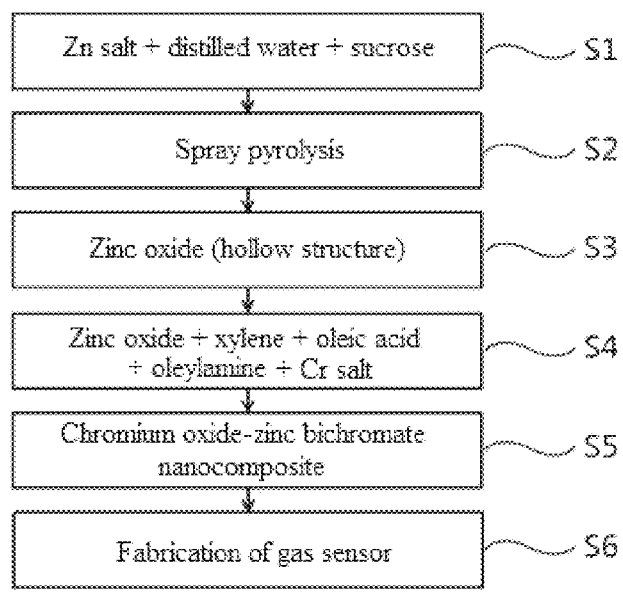
FIG. 1 is a flowchart schematically illustrating a method for preparing a gas sensing material for methylbenzene detection according to one embodiment of the present invention.

FIG. 1 is a flowchart schematically illustrating a method based on galvanic replacement. Referring to FIG. 1, the gas sensing material of the present invention is prepared by a method including a) preparing a solution including a Zn salt and a carbohydrate, b) subjecting the solution to spray pyrolysis to prepare a ZnO powder having a hollow structure, and c) mixing the ZnO powder with a Cr salt, followed by a galvanic replacement reaction to produce a nanocomposite of $Cr_2O_3$ and $ZnCr_2O_4$.

The nanocomposite prepared by the method contains 78.2 at. % to 90.0 at. % of Cr, based on the sum of the contents of Cr and Zn atoms.

In step a), the Zn salt may be ZnO and the carbohydrate may be selected from the group consisting of sucrose, glucose, and a mixture thereof. In step a), a predetermined amount of nitric acid ($HNO_3$) may be added. The nitric acid serves to assist in dissolving the Zn salt in the form of $Zn^{2+}$ in the aqueous solution through pH adjustment.

Subsequently, the solution of the Zn salt and the carbohydrate is subjected to spray pyrolysis. Specifically, in step b), the spray pyrolysis may be performed by spraying the solution at a rate of 5 L/min to 20 L/min into an electric furnace heated to 700° C. to 1000° C. If the spray pyrolysis temperature is lower than 700° C., the carbohydrate is incompletely thermally decomposed, leaving carbon components and residual organics in the composite. Meanwhile, if the spray pyrolysis temperature exceeds 1000° C., the solvent is volatilized very fast from the droplets, and as a result, the hollow structure collapses or the particles grow excessively, which is disadvantageous in gas sensitivity. If the spray rate of the solution is less than 5 L/min, the pyrolysis time increases, and as a result, the hollow structure collapses or the particles grow excessively, which is disadvantageous in gas sensitivity. Meanwhile, if the spray rate of the solution exceeds 20 L/min, the pyrolysis time decreases, and as a result, the carbohydrate is incompletely thermally decomposed, leaving carbon components in the composite.

After the spray pyrolysis, the ZnO powder is mixed with a Cr salt and the mixture is subjected to a galvanic replacement reaction to produce a nanocomposite of $Cr_2O_3$ and $ZnCr_2O_4$. Step c) includes i) dissolving the ZnO powder in xylene and heating the solution to 80° C. to 150° C., ii) adding oleylamine and oleic acid to the heated solution and stirring the resulting solution, iii) mixing the stirred solution with a Cr salt, followed by a galvanic replacement reaction.

The heating in step i) is performed to supply thermal energy for the migration of cations in the ZnO and the migration of Cr cations in the solution to initiate the subsequent galvanic replacement reaction. If the heating temperature is lower than 80° C., thermal energy necessary for the subsequent galvanic replacement reaction to proceed is not supplied. Meanwhile, if the heating temperature exceeds 150° C., a large amount of the xylene solvent is volatilized, and as a result, the amount of the xylene remaining in the reactor is considerably reduced, making it difficult for the subsequent galvanic replacement reaction to proceed. In step iii), the Cr salt may be $CrCl_2$.

Finally, the method of the present invention may further include, after step iii), washing and drying the $Cr_2O_3/ZnCr_2O_4$ nanocomposite and annealing the dried $Cr_2O_3/ZnCr_2O_4$ nanocomposite at 400° C. to 700° C. for 0.2 hours to 16 hours. The annealing is performed to remove a very small amount of residual organic matter and to form $Cr_2O_3/ZnCr_2O_4$ oxide interfaces. If the annealing temperature is lower than 400° C., residual organic matter is not sufficiently decomposed or uniform $Cr_2O_3/ZnCr_2O_4$ oxide interfaces are not formed. Meanwhile, if the annealing temperature exceeds 600° C., a secondary phase other than the two phases is formed by a reaction between the $Cr_2O_3/ZnCr_2O_4$ interfaces or the size of the particles increases, resulting in low gas response.

Alternatively, the gas sensing material for methylbenzene detection according to the present invention may be prepared by a method based on a solid-state reaction through calcination of a mixed powder. Specifically, the method includes a) mixing a Zn salt powder with a Cr salt powder and subjecting the powder mixture to ball milling to prepare a mixed powder and b) calcining the mixed powder at 1100° C. to 1300° C. for 4 hours to 6 hours to prepare a solid-state mix in the form of a fine powder.

According to the method based on a solid-state reaction, in step a), the Zn salt powder and the Cr salt powder are mixed in such amounts that the content of Cr is from 78.2 at. % to 90.0 at. %, based on the sum of the contents of Cr and Zn atoms. Within this range, high sensitivity and selectivity to methylbenzene gases can be achieved. Likewise in the previous method, the Zn salt may be ZnO and the Cr salt may be $Cr_2O_3$.

In step b), the powder mixture is preferably calcined at 1100° C. to 1300° C. for 4 hours to 6 hours. If the calcining temperature is lower than 1100° C., the desired $Cr_2O_3/ZnCr_2O_4$ phase is not formed. Meanwhile, if the calcining temperature exceeds 1300° C., a secondary phase other than the $Cr_2O_3/ZnCr_2O_4$ phase is formed or the size of the particles increases, resulting in low gas sensitivity.

As described above, the gas sensing material for methylbenzene detection according to the present invention can be prepared based on a galvanic replacement or solid-state reaction after the atom contents are adjusted to the predetermined ratio at the initial stage. Alternatively, a $ZnCr_2O_4$ nanocomposite and a commercial $Cr_2O_3$ fine powder having a different composition from that defined above are subjected to a solid-state reaction and then the atom contents are adjusted to the ratio defined above, which is described in Example 3 that follows.

Alternatively, the gas sensing material for methylbenzene detection according to the present invention may be prepared by a method based on spray pyrolysis. Specifically, the method includes a) preparing a solution including a Zn salt, a Cr salt, and a carbohydrate and b) subjecting the solution to spray pyrolysis to produce a nanocomposite of $Cr_2O_3$ and $ZnCr_2O_4$.

In step a), the Zn may be ZnO, the Cr salt may be $CrCl_2$, and the carbohydrate may be selected from the group consisting of sucrose, glucose, and a mixture thereof. In step a), a predetermined amount of nitric acid ($HNO_3$) may be added. The nitric acid serves to assist in dissolving the Zn salt in the form of $Zn^{2+}$ in the aqueous solution through pH adjustment.

The subsequent spray pyrolysis is performed as described above. The $Cr_2O_3/ZnCr_2O_4$ composite synthesized based on spray pyrolysis contains 68.0 at. % of Cr. Also in this case, the composite has high response and selectivity to methylbenzenes, indicating its applicability to a methylbenzene gas sensor even when the Cr content is 68.0 at. %.

According to the method based on spray pyrolysis, since droplets containing two ions are converted into oxides without a substantial change in composition, a mixed phase of $Cr_2O_3$ and $ZnCr_2O_4$ is formed even when $[Cr]/\{[Cr]+[Zn]\}$ is 68%.

The present invention also provides a gas sensor for methylbenzene detection, including a gas sensing layer composed of the gas sensing material. Specifically, the gas sensor of the present invention may be fabricated by a method including a) mixing the gas sensing material with deionized water to prepare a paste, b) coating the paste on a substrate, and c) drying and annealing the coated substrate to form a gas sensing layer.

The substrate may be an Au electrode-patterned alumina substrate and the coating may be performed by any suitable technique, such as drop coating.

In step c), the drying may be performed at 70° C. to 90° C. for 1 hour to 2 hours and the annealing may be performed at 400° C. to 600° C. for 0.5 hour to 24 hours.

The present invention will be explained in more detail with reference to the following examples. However, these examples are provided to assist in understanding the invention and are not intended to limit the scope of the invention.

Example 1

Preparation of Inventive as Sensing Material for Methylbenzene Detection and Fabrication of Inventive Gas Sensor for Methylbenzene Detection Including the Gas Sensing Material (1) FIG. 1 illustrates a method for preparing a gas sensing material for methylbenzene detection and a gas sensor including the gas sensing material according to embodiments of the present invention.

Referring to FIG. 1, first, 8.32 g of zinc oxide (ZnO, 99.99%, Sigma-Aldrich Co. Ltd), 34.20 g of sucrose ($C_{12}H_{22}O_{11}$, 99.5%, Sigma-Aldrich Co. Ltd), and 20 ml of nitric acid ($HNO_3$, 60.0%, Samchun Chemical Co.) were mixed in 980 mL of deionized water. The solution was stirred for 1 h. The stirred solution was placed in a nebulizer container made of an acrylic material and the container was mounted in a spray pyrolysis system. A Teflon collection net was installed in a particle collection chamber mounted at the bottom of the spray pyrolysis system. The solution was sprayed in the form of droplets through an oscillator having a frequency of 1.7 MHz under an air atmosphere. At this time, spray pyrolysis was allowed to proceed at a spray rate of 20 L/min into an electric furnace heated to 700□. After completion of the reaction, a pure ZnO powder having a hollow structure was collected through the Teflon collection net installed in the particle collection chamber.

0.03 g of the hollow ZnO powder was dissolved with stirring in 15 ml of xylene ($C_6H_4(CH_3)_2$, ACS reagent ≥98.5%, Sigma-Aldrich Co.) and heated to 90□. Thereafter, to the heated solution were added 0.75 g of oleylamine ($C_{18}H_{35}NH_2$, 70%, Sigma-Aldrich Co.) and 0.14 g of oleic acid ($C_{17}H_{33}COOH$, 90%, Sigma-Aldrich Co.). Stirring was continued until the resulting solution become homogenous. Next, 0.37 ml of a 2 M aqueous solution of chromium (II) chloride ($CrCl_2$, 99.99%, Sigma-Aldrich Co.) was added to the stirred solution. By the addition of the chromium (II) chloride, $[Cr]/\{[Cr]+[Zn]\}$ reached 81.9 at. %, as measured by ICP analysis. Thereafter, a galvanic replacement reaction was carried out over 2 h. The reaction solution was washed, dried, and annealed at 500□ over 2 h, giving a $Cr_2O_3/ZnCr_2O_4$ nanocomposite.

(2) The nanocomposite was mixed with deionized water, drop coated on an Au electrode-patterned alumina substrate, dried at 90□ for 2 h, and annealed at 400□ for 2 h, completing the fabrication of a gas sensor for methylbenzene detection.

The gas sensor was placed in a gas detection chamber made of a quartz tube. Pure air or a mixed gas were alternately fed into the chamber. A change in the resistance of the gas sensor was measured in real time. The gas concentration was adjusted to an optimal concentration through an MFC. The gas concentration in the gas detection chamber was changed by rapidly feeding the gas into the gas detection chamber through a 4-way valve. The total flow rate in the gas detection chamber was fixed to 200 sccm such that the temperature of the gas sensor was maintained constant despite the rapid change in gas concentration.

Example 2

Preparation of Inventive Gas Sensing Material for Methylbenzene Detection and Fabrication of Inventive Gas Sensor for Methylbenzene Detection Including the Gas Sensing Material (1) A chromium oxide powder ($Cr_2O_3$, powder, ≥98% metals basis, Sigma-aldrich Co.) and a zinc oxide powder (ZnO, nanopowder, <100 nm 99.9% metals basis, Sigma-aldrich Co.) were mixed in such amounts that the same ratio as described in Example 1 was reached ($[Cr]/\{[Cr]+[Zn]\}$=81.9 at. %, as measured by ICP analysis). The powder mixture was subjected to ball milling for ≥24 h. The mixed powder was calcined at 1100° C. for 4 h (a solid-state reaction method) to produce a $Cr_2O_3/ZnCr_2O_4$ solid-state mix in the form of a fine powder.

(2) The fine powder was mixed with deionized water, drop coated on an Au electrode-patterned alumina substrate, dried at 90° C. for 2 h, and annealed at 400° C. for 2 h, completing the fabrication of a gas sensor. Thereafter, the gas sensing characteristics of the sensor was measured by the same method as described in Example 1.

Example 3

Preparation of Inventive Gas Sensing Material for Methylbenzene Detection and Fabrication of Inventive Gas Sensor for Methylbenzene Detection Including the Gas Sensing Material (1) First, a ZnO powder having a hollow structure was produced in the same manner as in Example 1. 0.03 g of the hollow ZnO powder was dissolved with stirring in 15 ml of xylene ($C_6H_4(CH_3)_2$, ACS reagent ≥98.5%, Sigma-Aldrich Co.) and heated to 90□. Thereafter, to the heated solution were added 0.75 g of oleylamine ($C_{18}H_{35}NH_2$, 70%, Sigma-Aldrich Co.) and 0.14 g of oleic acid ($C_{17}H_{33}COOH$, 90%, Sigma-Aldrich Co.). Stirring was continued until the resulting solution become homogenous. Next, 0.18 ml of an aqueous solution of chromium chloride ($CrCl_2$, 99.99%, Sigma-Aldrich Co.) was added to the stirred solution. By the addition of the chromium chloride, [Cr]/{[Cr]+[Zn]} reached 77.9 at. %, as measured by ICP analysis. Thereafter, a galvanic replacement reaction was carried out over 2 h. The reaction solution was washed, dried, and annealed at 500° C. over 2 h, giving a single-phase $ZnCr_2O_4$ nanocomposite (Comparative Example 3).

Next, the single-phase $ZnCr_2O_4$ nanocomposite was mixed with a commercial chromium oxide powder ($Cr_2O_3$, powder, ≥98% metals basis, Sigma-Aldrich Co.) in such amounts that the same ratio as described in Example 1 was reached ([Cr]/{[Cr]+[Zn]}=81.9 at. %, as measured by ICP analysis). The powder mixture was subjected to ball milling for ≥24 h. The mixed powder was calcined at 1100° C. for 4 h (a solid-state reaction method) to produce a $Cr_2O_3$/$ZnCr_2O_4$ solid-state mix in the form of a fine powder.

(2) The fine powder was mixed with deionized water, drop coated on an Au electrode-patterned alumina substrate, dried at 90° C. for 2 h, and annealed at 400° C. for 2 h, completing the fabrication of a gas sensor. Thereafter, the gas sensing characteristics of the sensor was measured by the same method as described in Example 1.

Example 4

Preparation of Inventive Gas Sensing Material for Methylbenzene Detection and Fabrication of Inventive Gas Sensor for Methylbenzene Detection Including the Gas Sensing Material (1) First, 2.60 g of zinc oxide (ZnO, 99.99%, Sigma-Aldrich Co. Ltd), 8.36 g of chromium (II) chloride ($CrCl_2$, 99.99%, Sigma-Aldrich Co.), 34.02 g of sucrose ($C_{12}H_{22}O_{11}$, 99.5%, Sigma-Aldrich Co. Ltd), and 20 ml of nitric acid ($HNO_3$, 60.0%, Samchun Chemical Co.) were mixed in 980 mL of deionized water. The solution was stirred for 1 h. The stirred solution was placed in a nebulizer container made of an acrylic material and the container was mounted in a spray pyrolysis system. A Teflon collection net was installed in a particle collection chamber mounted at the bottom of the spray pyrolysis system. The solution was sprayed in the form of droplets through an oscillator having a frequency of 1.7 MHz under an air atmosphere. At this time, spray pyrolysis was allowed to proceed at a spray rate of 20 L/min into an electric furnace heated to 800° C. After completion of the reaction, a $Cr_2O_3$/$ZnCr_2O_4$ composite ([Cr]/{[Cr]+[Zn]}=68.0 at. %) was collected through the Teflon collection net installed in the particle collection chamber. Thereafter, annealing was conducted under an air atmosphere at 600° C. for 2 h to stabilize the phase and remove residual organic matter.

(2) The fine powder was mixed with deionized water, drop coated on an Au electrode-patterned alumina substrate, dried at 90° C. for 2 h, and annealed at 400° C. for 2 h, completing the fabrication of a gas sensor. Thereafter, the gas sensing characteristics of the sensor was measured by the same method as described in Example 1.

Comparative Example 1

Preparation of Conventional as Sensing Material (Hollow ZnO) for Methylbenzene Detection and Fabrication of Conventional Sensor (1) A ZnO powder having a hollow structure was produced in the same manner as described in Example 1 (S1-S3 in FIG. 1). The hollow ZnO powder was used as a gas sensing material for methylbenzene detection.

(2) The ZnO powder was mixed with deionized water, drop coated on an Au electrode-patterned alumina substrate, dried at 90° C. for 2 h, and annealed at 400° C. for 2 h, completing the fabrication of a gas sensor. Thereafter, the gas sensing characteristics of the sensor was measured by the same method as described in Example 1.

Comparative Example 2

Preparation of Conventional Gas Sensing Material ($Cr_2O_3$ Powder) for Methylbenzene Detection and Fabrication of Conventional Sensor A commercial chromium oxide powder ($Cr_2O_3$, powder, ≥98% metals basis, Sigma-Aldrich Co.) was mixed with deionized water, drop coated on an Au electrode-patterned alumina substrate, dried at 90° C. for 2 h, and annealed at 400° C. for 2 h, completing the fabrication of a gas sensor. Thereafter the gas sensing characteristics of the sensor was measured by the same method as described in Example 1.

Comparative Example 3

Preparation of Conventional Gas Sensing Material (Single-Phase $ZnCr_2O_4$ Nanocomposite) for Methylbenzene Detection (1) A gas sensing material was prepared and a gas sensor was fabricated according to the entire procedure (S1-S6) illustrated in FIG. 1. First, a ZnO powder having a hollow structure was produced in the same manner as in Example 1. 0.03 g of the hollow ZnO powder was dissolved with stirring in 15 ml of xylene ($C_6H_4(CH_3)_2$, ACS reagent ≥98.5%, Sigma-Aldrich Co.) and heated to 90□. Thereafter, to the heated solution were added 0.75 g of oleylamine ($C_{18}H_{35}NH_2$, 70%, Sigma-Aldrich Co.) and 0.14 g of oleic acid ($C_{17}H_{33}COOH$, 90%, Sigma-Aldrich Co.). Stirring was continued until the resulting solution become homogenous. Next, 0.18 ml of a 2 M aqueous solution of chromium chloride ($CrCl_2$, 99.99%, Sigma-Aldrich Co.) was added to the stirred solution. By the addition of the chromium chloride, [Cr]/{[Cr]+[Zn]} reached 77.9 at. %, as measured by ICP analysis. Thereafter, a galvanic replacement reaction was carried out over 2 h. The reaction solution was washed, dried, and annealed at 500° C. over 2 h, giving a single-phase $ZnCr_2O_4$ nanocomposite.

(2) The fine powder was mixed with deionized water, drop coated on an Au electrode-patterned alumina substrate, dried at 90° C. for 2 h, and annealed at 400° C. for 2 h, completing the fabrication of a gas sensor. Thereafter, the gas sensing characteristics of the sensor was measured by the same method as described in Example 1.

Experimental Example 1

The gas sensors of Examples 1-3 and Comparative Examples 1-3 were measured for gas sensing characteristics toward ethanol, methylbenzenes (xylene and toluene), benzene, HCHO, and CO, which correspond to indoor environmental gases, at five different temperatures of 250° C., 275° C., 300° C., 325° C., and 350° C. The gas sensors of Examples 1-3 and Comparative Examples 2 and 3 showed p-type oxide semiconductor sensing behavior toward the reducing gases, where their resistance was increased.

In contrast, the gas sensor of Comparative Example 1 showed n-type oxide semiconductor sensing behavior toward the reducing gases, where their resistance was reduced. Accordingly, the gas response of each of the gas sensors of Examples 1-2 and Comparative Examples 2-3 showing p-type oxide semiconductor sensing behavior toward the reducing gases was given by $R_g/R_a$ (where $R_g$ is the resistance of the sensor in the gas and $R_a$ is the resistance of the sensor in air). In contrast, the gas response of the gas sensor of Comparative Example 1 was given by $R_a/R_g$. The response of each gas sensor to xylene ($S_{xylene}$) and an interfering gas ($S_{gas}$) were measured and the selectivity of the gas sensor to xylene was calculated from the response ratio ($S_{xylene}/S_{gas}$).

When the resistance of the sensor in air reached a constant state ($R_a$), a test gas (5 ppm ethanol, xylene, toluene, benzene, HCHO or CO) was allowed to flow into a gas chamber to change the atmosphere of the gas chamber. When the resistance of the sensor in the gas was kept constant ($R_g$), the atmosphere of the gas chamber air was changed by a flow of air. At this time, changes in resistance were measured.

Experimental Example 2

X-Ray Diffraction Analysis for the Inventive Gas Sensing Materials

Figure 2:
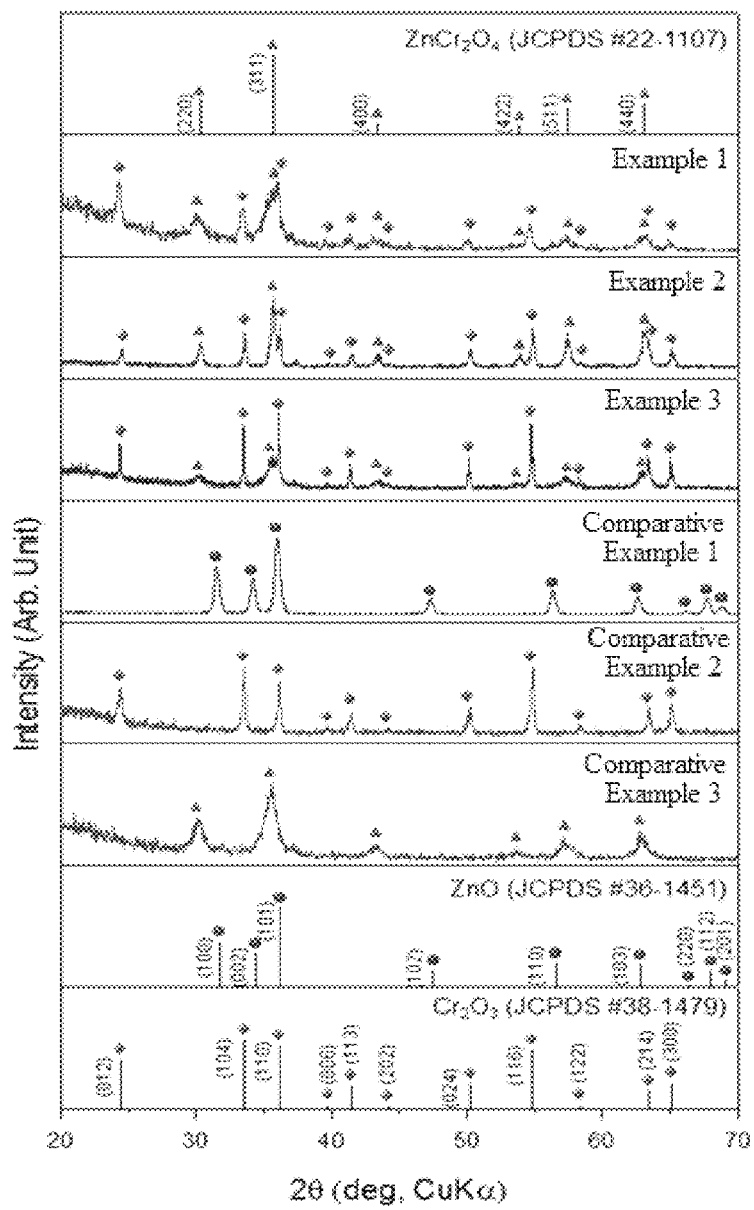
FIG. 2 shows the results of X-ray diffraction analysis for gas sensing materials prepared in Comparative Examples 1 to 3 and Examples 1 to 3.

FIG. 2 shows the results of X-ray diffraction analysis for the gas sensing materials of Example 1 ($Cr_2O_3/ZnCr_2O_4$ nanocomposite prepared based on spray pyrolysis), Example 2 (commercial $Cr_2O_3/ZnCr_2O_4$ fine powder solid-state mix), Example 3 (commercial $Cr_2O_3/ZnCr_2O_4$ fine powder/nanocomposite solid-state mix), Comparative Example 1 (ZnO powder having hollow structure), Comparative Example 2 (commercial $Cr_2O_3$ fine powder), and Comparative Example 3 ($ZnCr_2O_4$ nanocomposite).

Referring to FIG. 2, the gas sensing material of Example 1 had a pattern of the nanocomposite in which $Cr_2O_3$ and $ZnCr_2O_4$ were mixed in the predetermined ratio. The X-ray diffraction pattern of the gas sensing material of Example 2 shows that $Cr_2O_3$ and $ZnCr_2O_4$ were mixed in the predetermined ratio. The gas sensing materials of Comparative Examples 1-3 were found to have diffraction patterns corresponding to ZnO, $Cr_2O_3$, and $ZnCr_2O_4$, respectively. The X-ray diffraction pattern of the gas sensing material of Example 3 confirms the presence of $Cr_2O_3$ because $Cr_2O_3$ was further added to and mixed with $ZnCr_2O_4$. The X-ray diffraction patterns confirm that the $ZnCr_2O_4$ composite was produced by galvanic replacement of the mixture of the hollow ZnO and the Cr salt and the $Cr_2O_3/ZnCr_2O_4$ was produced when the Cr salt was present in a sufficient amount.

Experimental Example 3

Secondary Particle Structures of the Inventive Gas Sensing Materials

Figure 3:
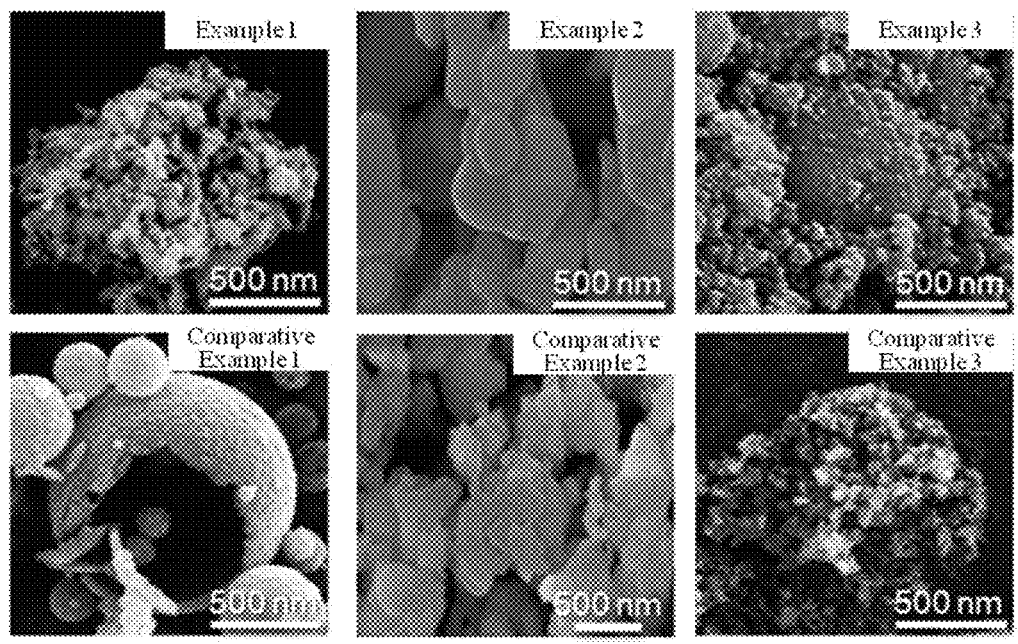
FIG. 3 shows SEM images of the secondary particle structures of gas sensing materials prepared in Comparative Examples 1 to 3 and Examples 1 to 3.

FIG. 3 shows SEM images of the secondary particle structures of the gas sensing materials synthesized in Example 1 ($Cr_2O_3/ZnCr_2O_4$), Example 2 (commercial $Cr_2O_3/ZnCr_2O_4$ fine powder solid-state mix), Example 3 (commercial $Cr_2O_3/ZnCr_2O_4$ fine powder/nanocomposite solid-state mix), Comparative Example 1 (ZnO), Comparative Example 2 ($Cr_2O_3$), and Comparative Example 3 ($ZnCr_2O_4$).

Referring to FIG. 3, the gas sensing material (ZnO) of Comparative Example 1 was found to maintain its hollow structure because when the solution containing the metal salt and sucrose was sprayed from the nebulizer for spray pyrolysis, the sucrose was rapidly decomposed at the high temperature in the electric furnace and the metal salt particles helped oxidize the sucrose while maintaining the hollow structure. The gas sensing materials of Example 1 and Comparative Example 3, which were prepared by galvanic replacement of the gas sensing material of Comparative Example 1, failed to maintain their hollow structures during replacement. The collapsed sensing materials existed in the form of oxide particles. Particularly, $Cr_2O_3$ secondary particles were mixed with $ZnCr_2O_4$ secondary particles in the nanocomposite of Example 1. In conclusion, the use of galvanic replacement enables rapid low-temperature synthesis of $ZnCr_2O_4$, which have been synthesized at a high temperature of ≥1100° C. for ≥4 h based on a solid-state mixing method.

Experimental Example 4

TEM Images of the Inventive as Sensing Materials

Figure 4A:
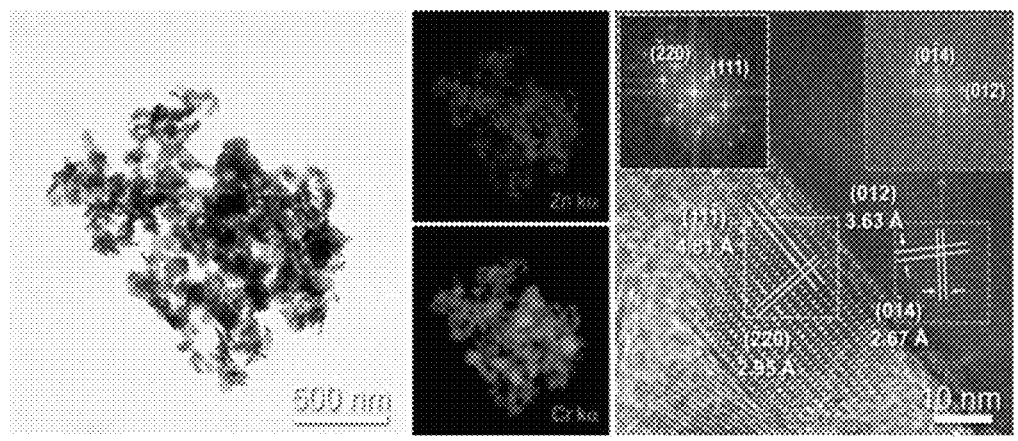
FIGS. 4a to 4c are TEM images of gas sensing materials prepared in Example 1 and Comparative Examples 1 and 3, respectively.
Figure 4B:
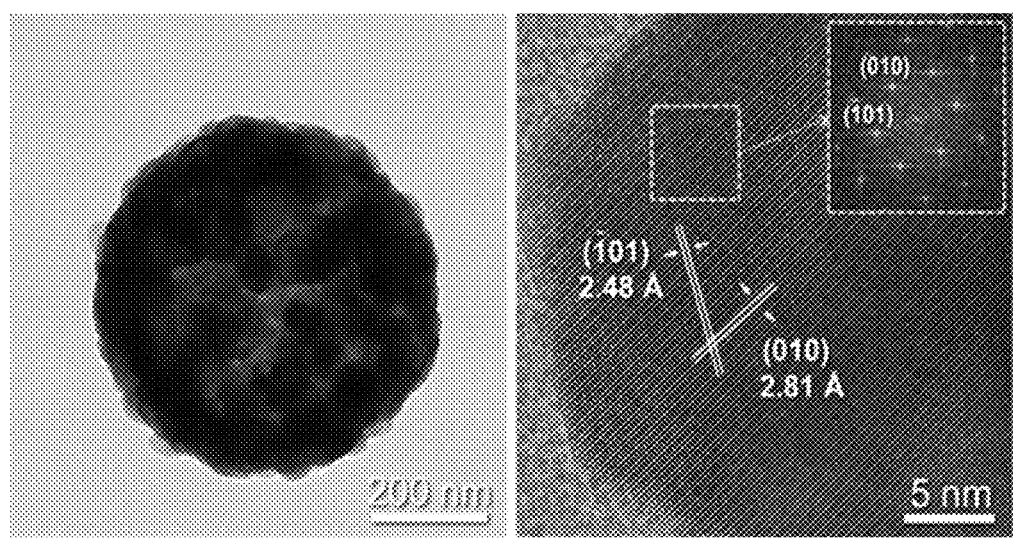
Figure 4C:
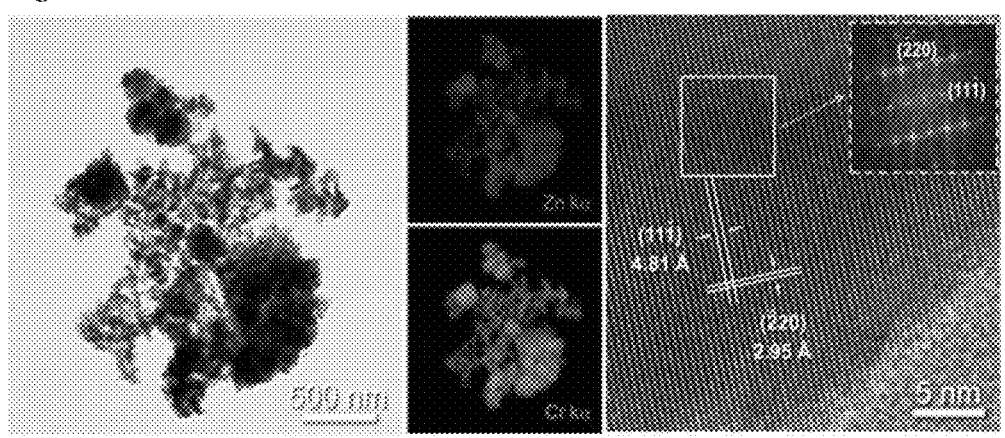
Figure 5A:
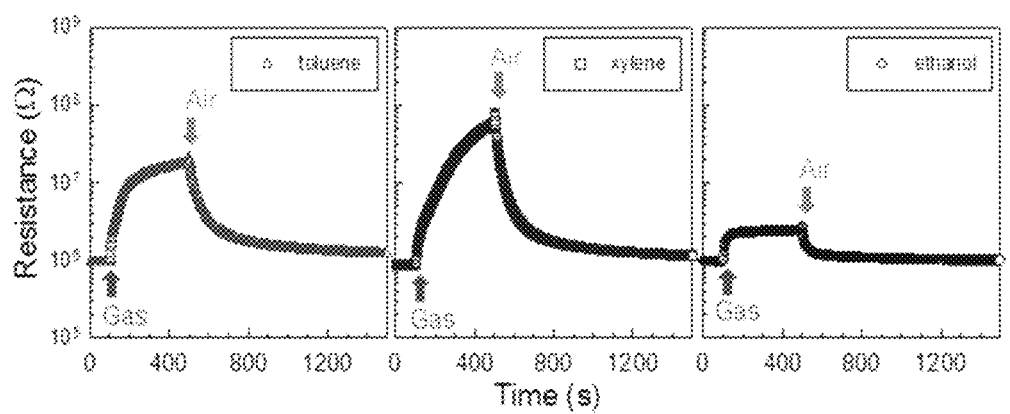
FIGS. 5a to 5f show the dynamic gas sensing characteristics of gas sensing materials prepared in Examples 1 to 3 and Comparative Examples 1 to 3 toward toluene, xylene, and ethanol (each 5 ppm) at an operating temperature of 275□, respectively.
Figure 5B:
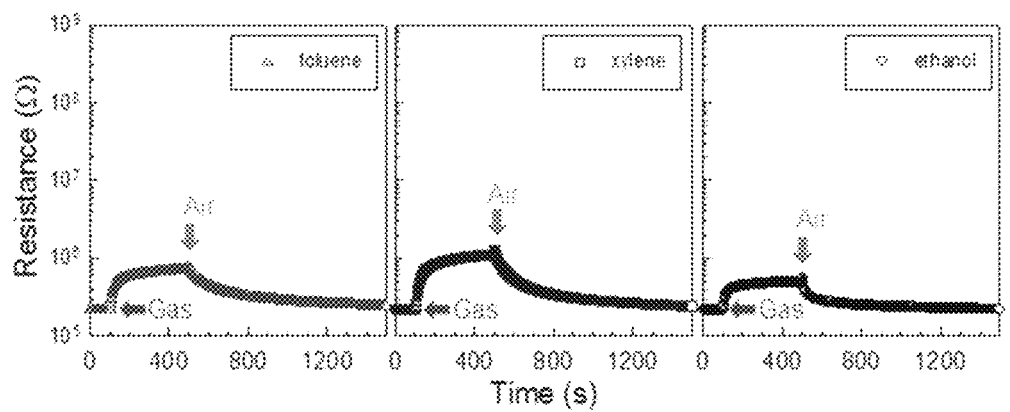
Figure 5C:
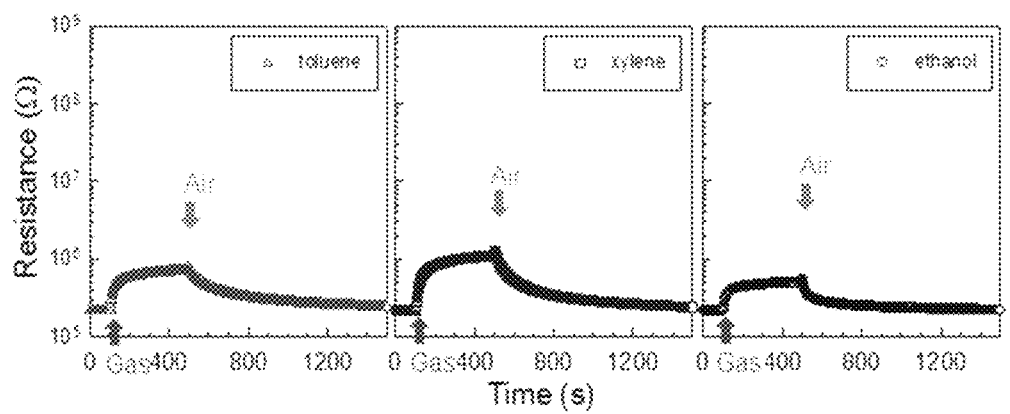
Figure 5D:
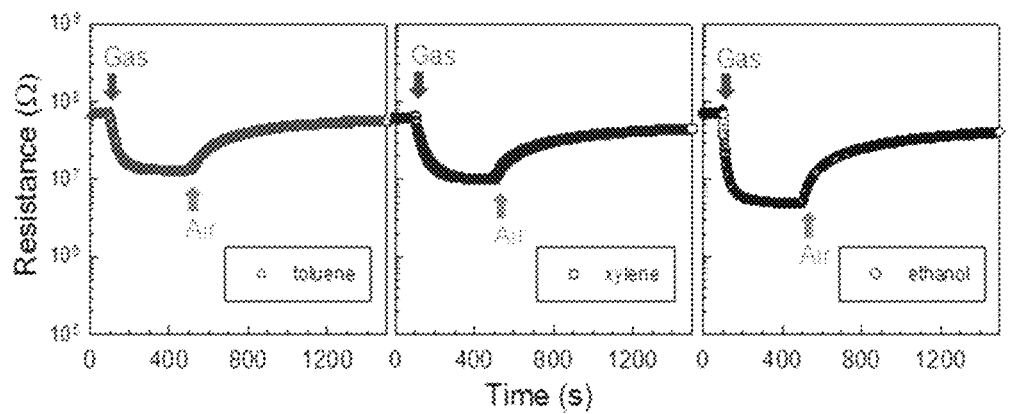
Figure 5E:
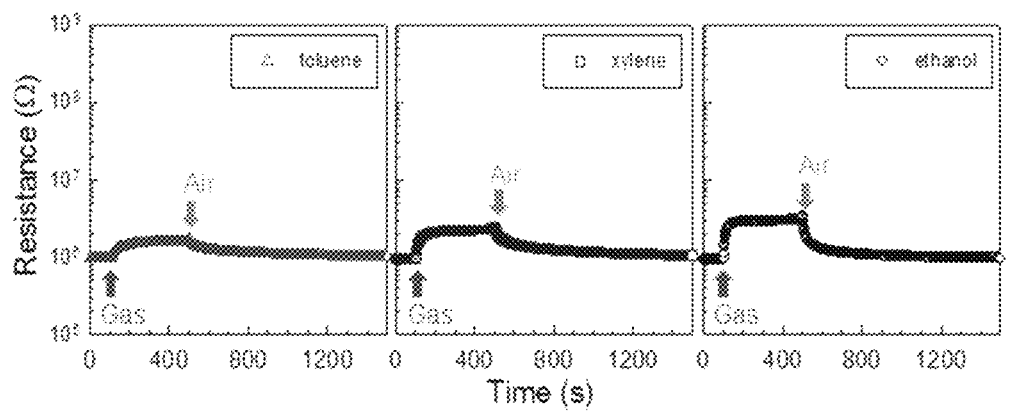
Figure 5F:
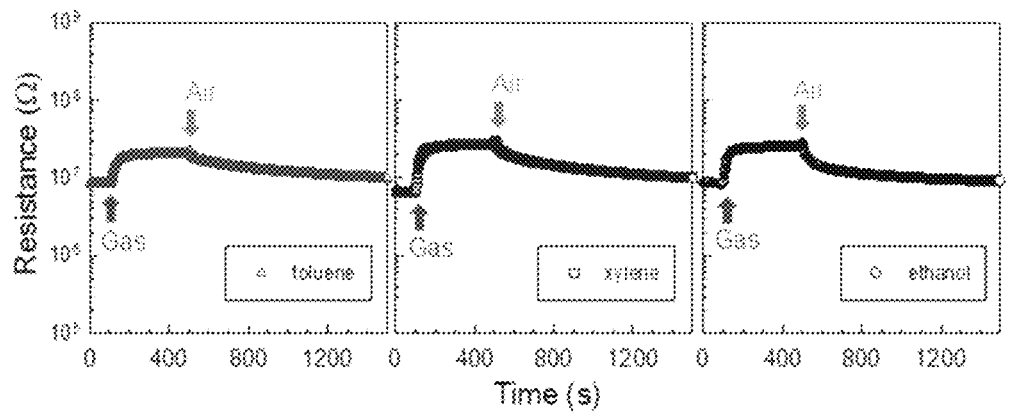

FIGS. 4a to 4c are TEM images of the gas sensing materials prepared in Example 1 and Comparative Examples 1 and 3, respectively.

The image (FIG. 4a) and elemental analysis of the gas sensing material of Example 1 reveal a uniform distribution of Cr and Zn. Lattice imaging reveals that the sensing material is a composite of $Cr_2O_3$ and $ZnCr_2O_4$. The image (FIG. 4b) of the gas sensing material of Comparative Example 1 shows that ZnO maintained its hollow structure. The image (FIG. 4c) of the gas sensing material of Comparative Example 3 shows the presence of $ZnCr_2O_4$ only.

Experimental Example 5

Dynamic Gas Sensing Characteristics of the Inventive as Sensing Materials Toward Toluene, Xylene, and Ethanol (Each 5 ppm)

FIGS. 5a to 5f show the dynamic gas sensing characteristics of the gas sensing materials prepared in Examples 1 to 3 and Comparative Examples 1 to 3 toward toluene, xylene, and ethanol (each 5 ppm) at an operating temperature of 275° C., respectively.

The gas sensing material having a hollow structure synthesized in Comparative Example 1 was found to show n-type gas sensing behavior toward toluene, xylene, and ethanol. The gas sensing materials other than the gas sensing material of Comparative Example 1 showed p-type gas sensing behavior.

Experimental Example 6

Figure 6:
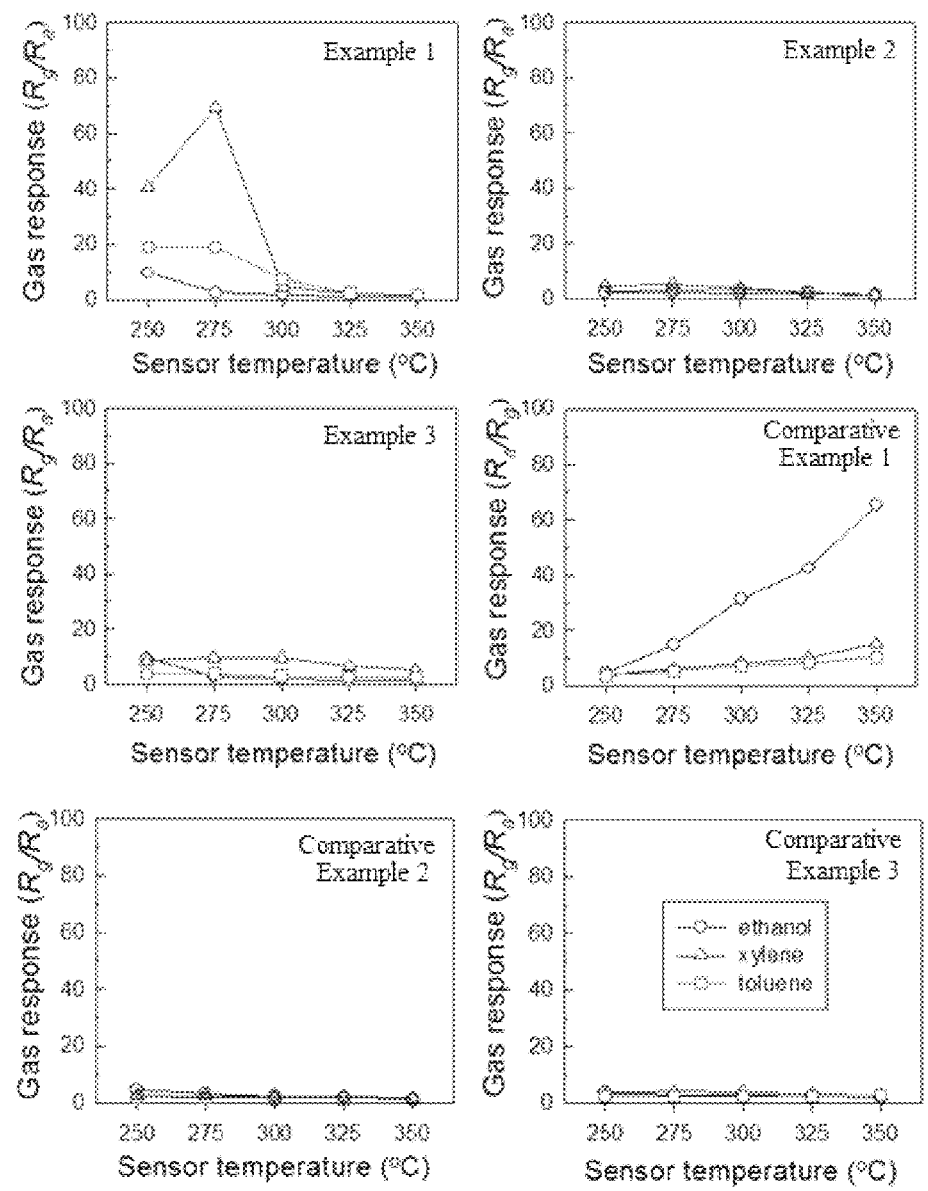
FIG. 6 shows the gas response of gas sensors fabricated in Examples 1 to 3 and Comparative Examples 1 to 3 to toluene, xylene, and ethanol gases at different operating temperatures.

Gas Responses of the Inventive as Sensors to Toluene, Xylene, and Ethanol Gases at Different Operating Temperatures FIG. 6 shows the gas responses of the gas sensors fabricated in Examples 1 to 3 and Comparative Examples 1 to 3 to toluene, xylene, and ethanol gases at different operating temperatures.

The gas responses of the gas sensor including the hollow ZnO synthesized in Comparative Example 1 to the gases were found to increase with increasing operating temperature. Particularly, the gas sensor of Comparative Example 1 showed a high response of 65.4 to 5 ppm ethanol gas.

The gas sensor fabricated based on galvanic replacement in Example 1 showed responses of 70.7, 18.9, and 2.6 to xylene, toluene, and ethanol (each 5 ppm) at 275° C., respectively, demonstrating its high responses to the methylbenzene gases. Particularly, considering that the response of the gas sensor of Example 1 to xylene gas was 27.2 times higher than that to ethanol gas, the gas sensor is advantageous in selective methylbenzene detection, which demonstrates that the gas sensor can be sufficiently used for the detection of indoor pollutant gases.

The gas sensors of Example 2 and Comparative Examples 2-3 showed relatively low gas responses of ≤10. The response of the gas sensors of Example 2 and Comparative Examples 2-3 to methylbenzenes were ≤3. The gas sensors of Examples 2-3 had lower responses than the gas sensor of Example 1 but showed sufficiently high selectivities to xylene. Accordingly, the gas sensors of Examples 2-3 are expected to be applicable to practical use. In contrast, none of the gas sensors of Comparative Examples 2-3 showed selectivities to the gases.

These results conclude that $Cr_2O_3/ZnCr_2O_4$ has high selectivity to xylene irrespective of its synthesis method so long as the Cr content is in the range of 78.2-90.0 at. %. Particularly, it can be concluded that the use of galvanic replacement is more effective for higher sensitivity and selectivity.

Experimental Example 7

Gas Sensing Characteristics of the as Sensor of Example 1 to Ethanol, Xylene, Toluene, Benzene, HCHO, and CO at Operating Temperature of 275 □

Figure 7:
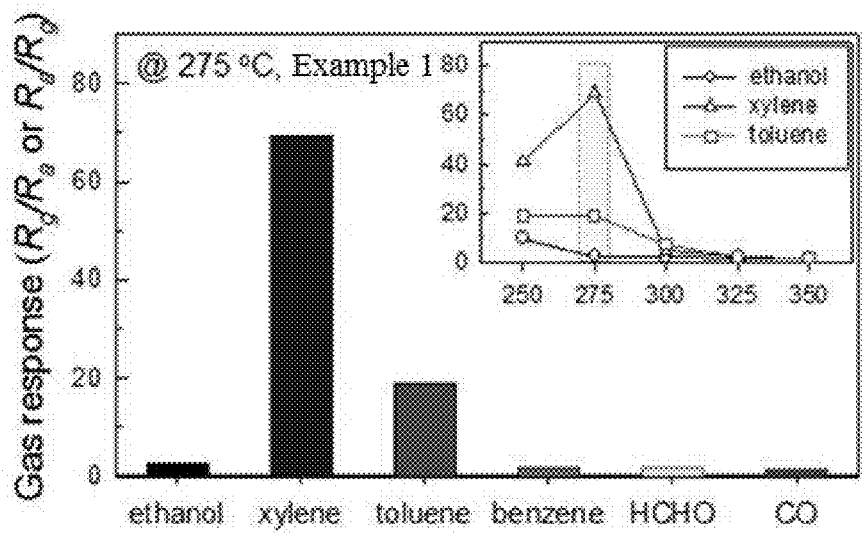
FIG. 7 shows the gas sensing characteristics of a gas sensor fabricated in Example 1 to ethanol, xylene, toluene, benzene, HCHO, and CO at an operating temperature of 275□.

FIG. 7 shows the gas sensing characteristics of the gas sensor fabricated in Example 1 to ethanol, xylene, toluene, benzene, HCHO, and CO at an operating temperature of 275° C. FIG. 7 reveals high selectivities of the gas sensor of Example 1 to the methylbenzenes over ethanol. In addition, the gas sensor of Example 1 showed very high selectivities to the methylbenzenes over other indoor environmental gases.

The high selectivities of the gas sensor of Example 1 are believed to be because the composition of the $Cr_2O_3/ZnCr_2O_4$ nanocomposite synthesized based on galvanic replacement ($[Cr]/\{[Cr]+[Zn]\}$=81.9 at. %, as measured by ICP analysis) is advantageous in detecting methylbenzenes. Therefore, galvanic replacement is an improved approach to maximize the catalytic activities of $Cr_2O_3$ and $ZnCr_2O_4$ for the oxidation of xylene and toluene.

When the gas sensing results obtained by the gas sensor of Example 1 were compared with those obtained by the gas sensors of Comparative Examples 2-3, it can again be confirmed that the composition of the composite prepared in Example 1 ensures high xylene selectivity and sensitivity, which could not be achieved by single-phase $Cr_2O_3$ and $ZnCr_2O_4$.

The gas sensing material synthesized based on galvanic replacement in Example 1 was found to be more advantageous in detecting methylbenzenes than $Cr_2O_3/ZnCr_2O_4$ synthesized based on a solid-state synthesis method in Example 2. The enhanced methylbenzene response and selectivity of the gas sensing material of Example 1 are thought to arise from galvanic replacement for the synthesis of the $Cr_2O_3/ZnCr_2O_4$ composite in the form of a fine powder. That is, the replacement reaction proceeds uniformly in the fine powder to synthesize a single-phase $ZnCr_2O_4$ fine powder having a small particle size at low temperature and allows the formation of homogeneous p-p heterojunctions over the entire region of the sensing material to maximize the electrical sensitivity, which enhance the methylbenzene sensitivity and selectivity of the gas sensing material. The same can also be found in Example 3. This provides evidence for the formation of more homogenous p-p heterojunctions in the $ZnCr_2O_4$ fine powder having a smaller size.

Experimental Example 8

Cr Content of the Inventive $Cr_2O_3/ZnCr_2O_4$ Nanocomposite

Figure 8:
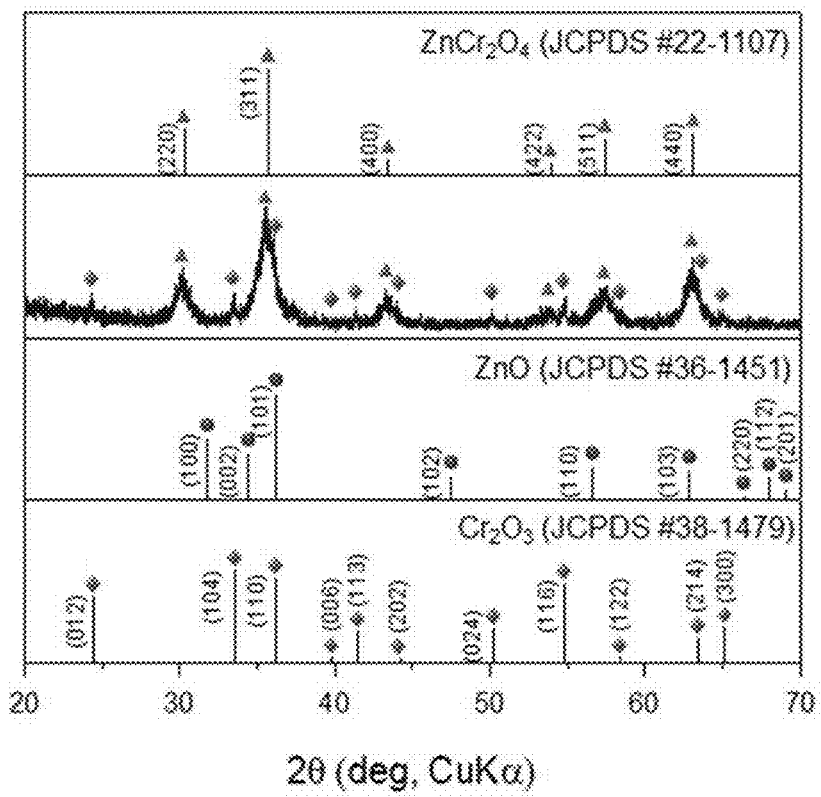
FIG. 8 shows the results of X-ray diffraction analysis for a $Cr_2O_3/ZnCr_2O_4$ nanocomposite, which was synthesized in the same manner as in Example 1 except that the content of Cr was changed such that $[Cr]/\{[Cr]+[Zn]\}$ was 78.2 at. %, as measured by ICP analysis.

A $Cr_2O_3/ZnCr_2O_4$ nanocomposite was synthesized in the same manner as in Example 1, except that the content of Cr was changed such that $[Cr]/\{[Cr]+[Zn]\}$ was 78.2 at. %, as measured by ICP analysis. FIG. 8 shows the results of X-ray diffraction analysis for the $Cr_2O_3/ZnCr_2O_4$ nanocomposite.

FIG. 8 reveals that when Cr was added in an amount corresponding to 78.2 at. %, a diffraction phase of $Cr_2O_3$ was present in a very small amount. In addition, it can be concluded that catalytic activity of $Cr_2O_3$ can be expected when Cr is present in an amount of ≥78.2 at. % in the $Cr_2O_3/ZnCr_2O_4$ nanocomposite. From these results, the lower limit of the content of Cr in the $Cr_2O_3/ZnCr_2O_4$ nanocomposite can be determined.

Experimental Example 9

Figure 9:
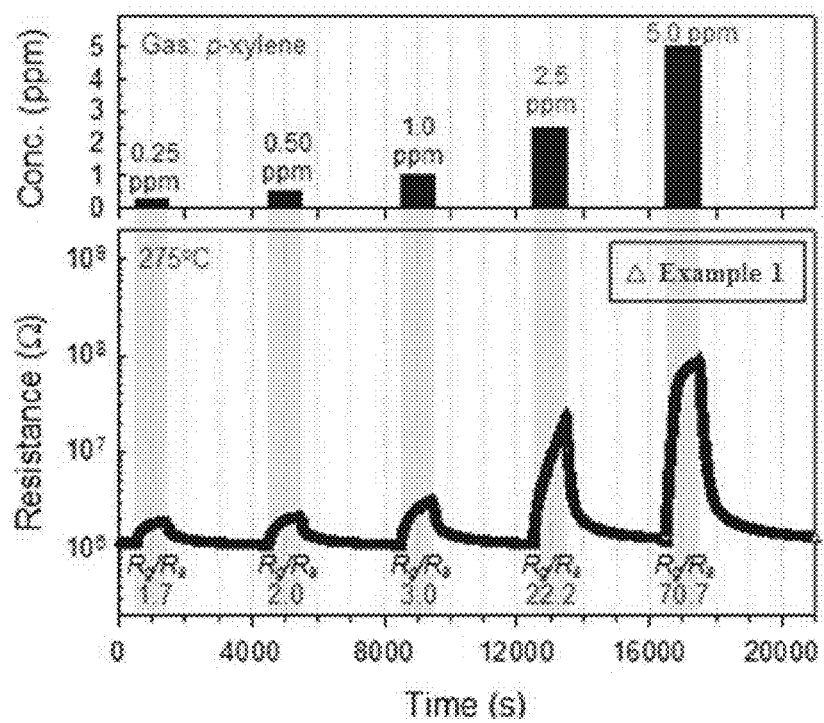
FIG. 9 shows the gas sensing characteristics of a gas sensor fabricated in Example 1 to xylene with varying concentrations of the gas.

Gas Sensing Characteristics of the as Sensor of Example 1 to Xylene with Varying Concentrations of the Gas FIG. 9 shows the gas sensing characteristics of the gas sensor fabricated in Example 1 to xylene with varying concentrations of the gas. The gas sensor showed high responses of 1.7, 2.0, 3.0, 22.2, and 70.7 to 50 ppb, 100 ppb, 250 ppb, 500 ppb, and 1 ppm ethanol gas at an operating temperature of 275° C., respectively. These results demonstrate high response of the gas sensor to xylene at the concentration level of 250 ppb, suggesting that the gas sensor can be effectively applied to the detection of indoor methylbenzenes at concentrations of ≤10 ppm, which is the object of the present invention.

Figure 10:
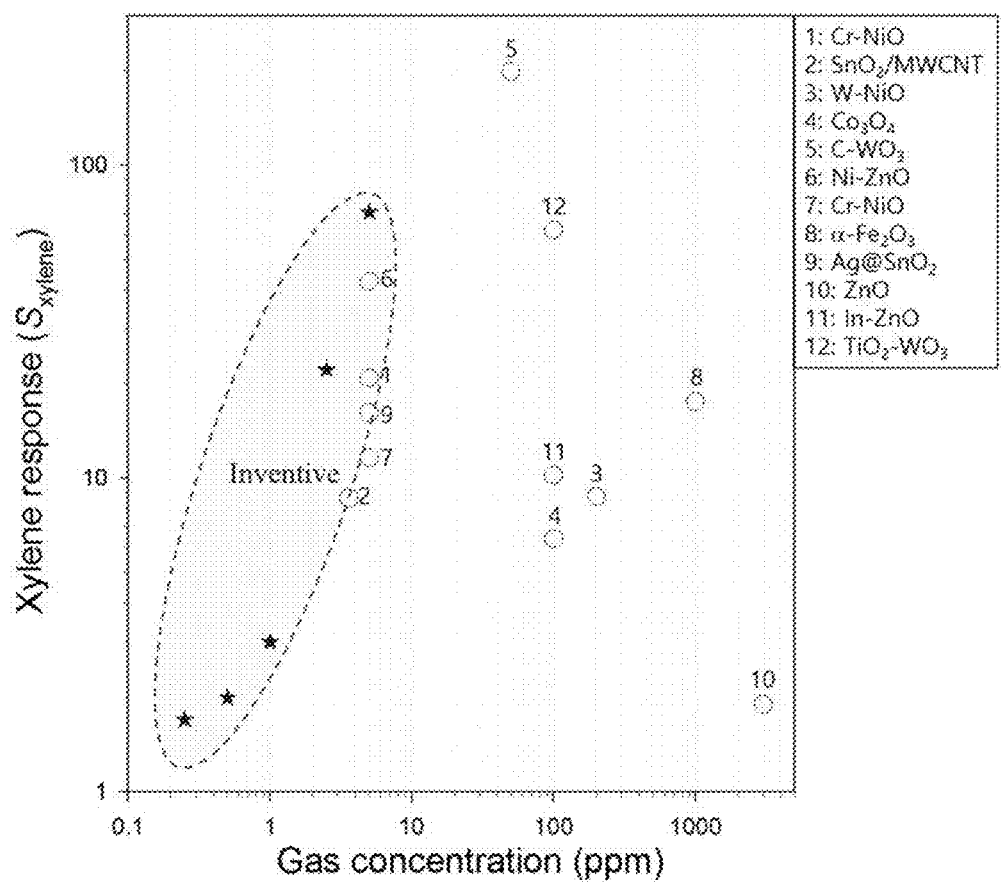
FIG. 10 compares the xylene response of an inventive gas sensing material to xylene at different concentrations with those of gas sensing materials reported in the literature.
Figure 11:
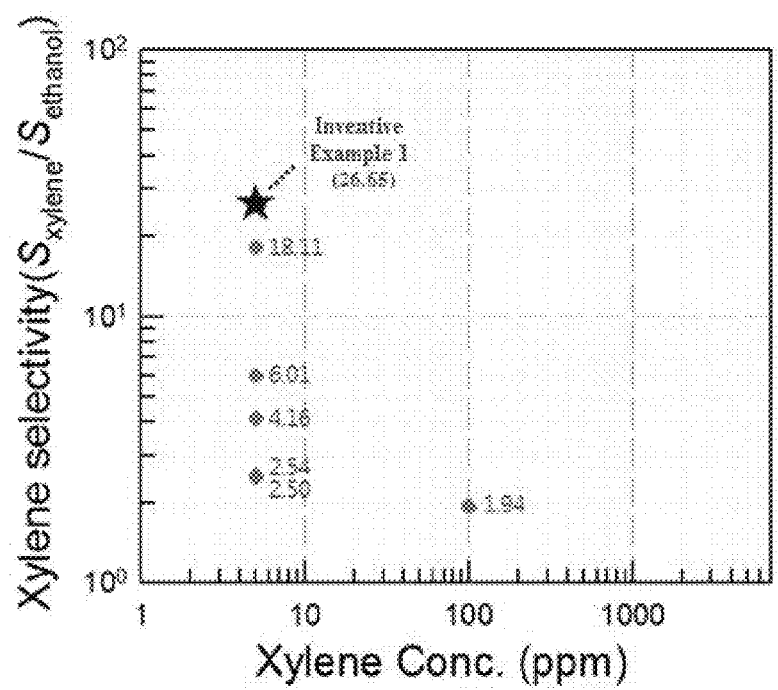
FIG. 11 compares the selectivity of a gas sensing material prepared in Example 1 to xylene over ethanol with those of gas sensing materials reported in the literature.

The responses of the gas sensing material of Example 1 to xylene at different concentrations and the selectivity of the gas sensing material of Example 1 to xylene over ethanol were compared with those of gas sensing materials reported in the literature. The results are shown in FIGS. 10 and 11. Referring to FIGS. 10 and 11, the gas sensing material of Example 1 showed much higher responses and selectivity to xylene at lower concentrations than gas sensing materials reported in the literature. The gas sensing material of Example 1 was found to effectively detect low concentrations of xylene compared to $SnO_2$ and $CO_3O_4$, which are generally known to have high methylbenzene responses. The inventive gas sensor was compared with conventional $ZnCr_2O_4$ gas sensors reported in the literature. As a result, the conventional gas sensors were found to show limited responses to ethanol and $Cl_2$ only. It is also difficult to conclude that the selectivities of the conventional gas sensors have significantly high selectivities. In contrast, the inventive $Cr_2O_3/ZnCr_2O_4$ nanocomposite prepared based on galvanic replacement showed significantly high responses and selectivities to methylbenzenes. Therefore, the inventive gas sensor is a highly sensitive and selective oxide semiconductor gas sensor to methylbenzenes.

Experimental Example 10

Humidity Stability of the as Sensor of Example 1

Figure 12:
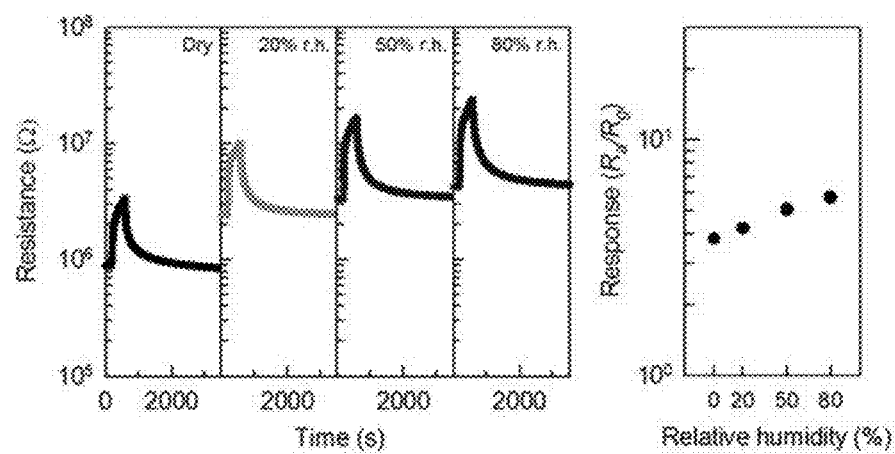
FIG. 12 shows the gas response of a gas sensor (275□) fabricated in Example 1 to 1 ppm xylene gas at relative humidities of 20%, 50%, and 80%.

FIG. 12 shows the responses of the gas sensor (275° C.) fabricated in Example 1 ($Cr_2O_3/ZnCr_2O_4$ ([Cr]/[Cr]+[Zn] =81.9 at %)) to 1 ppm xylene gas under humid conditions (20%, 50%, and 80% RH) rather than in a dry atmosphere.

The sensor of Example 1 did not undergo a reduction in response in a humid atmosphere, i.e. with increasing relative humidity (20%, 50%, and 80% RH), as well as in a dry atmosphere. These results demonstrate that the inventive gas sensor can be applied to the detection of methylbenzenes even in a humid atmosphere, which could not be achieved by conventional oxide semiconductor gas sensors. The high response of the inventive gas sensor to xylene in a humid atmosphere was maintained, suggesting that the inventive gas sensor is suitable for use in daily life.

Experimental Example 11

Cr Contents of the Inventive Gas Sensing Materials for Methylbenzene Detection

Galvanic replacement employed in Examples 1-3 is a method in which oxides are replaced by dissimilar metal salts to form composites. According to this method, there may be a difference between the amount of metal salts added and the amount of metal salts replaced. Thus, the results of ICP analysis for final composites may be significantly different from the amount of metal salts added. The contents of Cr in the Cr-added $Cr_2O_3/ZnCr_2O_4$ composite (Example 1) and the Cr-free single-phase $ZnCr_2O_4$ composite (Example 3) synthesized based on galvanic replacement were 81.9 at. % and 77.9 at. %, respectively, as measured by ICP analysis.

The Cr content of the Cr-added $Cr_2O_3/ZnCr_2O_4$ composite synthesized based on spray pyrolysis in Example 4 was 68.0 at. %. Since droplets containing two ions were converted into oxides during spray pyrolysis without a substantial change in composition, a mixed phase of $Cr_2O_3$ and $ZnCr_2O_4$ was formed even when [Cr]/{[Cr]+[Zn]} was 68%.

Figure 13:
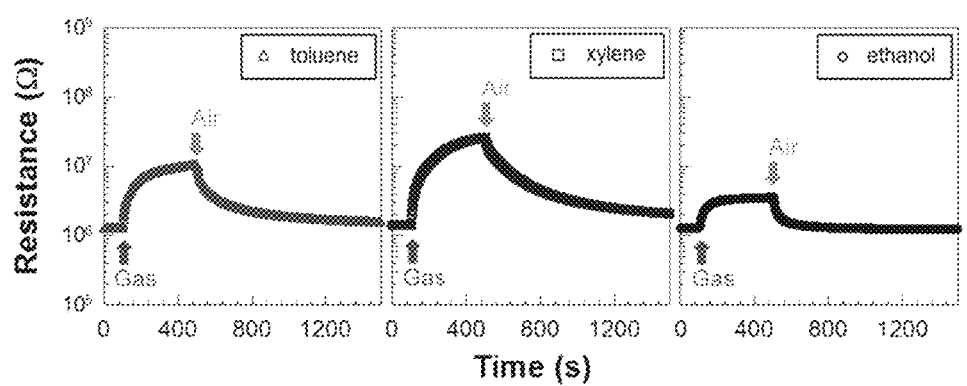
FIG. 13 shows the gas sensing characteristics of a $Cr_2O_3/ZnCr_2O_4$ composite sensor containing 68.0 at. % of Cr, which was synthesized based on spray pyrolysis in Example 4, toward toluene, xylene, and ethanol gases (each 5 ppm) at 275□.

FIG. 13 shows the gas sensing characteristics of the $Cr_2O_3/ZnCr_2O_4$ composite sensor containing 68.0 at. % of Cr, which was synthesized based on spray pyrolysis, toward gases (each 5 ppm) in a dry atmosphere at 275° C. The gas sensing characteristics of the gas sensor toward toluene, xylene, and ethanol gases (each 5 ppm) were measured. The responses of the gas sensor to toluene ($S_{toluene}$), xylene ($S_{xylene}$), and ethanol ($S_{ethonal}$) were found to be 8.1, 18.3, and 2.7, respectively, confirming high responses and selectivities of the gas sensor to the methylbenzenes. These results can lead to the conclusion that the gas sensor can be applied to the detection of methylbenzenes even when the Cr content is 68.0 at. %.

What is claimed is:

1. A gas sensing material for methylbenzene detection, comprising a nanocomposite of $Cr_2O_3$ and $ZnCr_2O_4$ wherein the content of Cr in the nanocomposite is from 67.0 at. % to 90.0 at. %, based on the sum of the contents of Cr and Zn atoms.

2. A gas sensor for methylbenzene detection, comprising a gas sensing layer composed of the gas sensing material according to claim 1.

3. A method for fabricating a gas sensor for methylbenzene detection, comprising a) mixing the gas sensing material according to claim 1 with deionized water to prepare a paste, b) coating the paste on a substrate, and c) drying and annealing the coated substrate to form a gas sensing layer.

4. The method according to claim 3, wherein the substrate is an Au electrode-patterned alumina substrate and the coating is performed by drop coating.

5. The method according to claim 3, wherein the drying is performed at 70° C. to 90° C. for 1 hour to 2 hours and the annealing is performed at 400° C. to 600° C. for 0.5 hour to 24 hours.

* * * * *